(12) United States Patent
Ouzounian

(10) Patent No.: US 7,542,991 B2
(45) Date of Patent: Jun. 2, 2009

(54) COMPUTERIZED HAZARDOUS MATERIAL RESPONSE TOOL

(76) Inventor: Gregory A. Ouzounian, 4061 E. Castro Valley Blvd., #224, Castro Valley, CA (US) 94552

( * ) Notice: Subject to any disclaimer, the term of this patent is extended or adjusted under 35 U.S.C. 154(b) by 914 days.

(21) Appl. No.: 10/843,757

(22) Filed: May 11, 2004

(65) Prior Publication Data
US 2005/0004770 A1      Jan. 6, 2005

Related U.S. Application Data

(60) Provisional application No. 60/469,272, filed on May 12, 2003.

(51) Int. Cl.
*G06F 17/00* (2006.01)

(52) U.S. Cl. .................. 707/104.1; 707/10; 707/101; 707/102; 707/103 Y; 702/2

(58) Field of Classification Search ............ 707/101, 707/102, 103 Y, 104.1, 10; 362/401; 705/28; 702/2
See application file for complete search history.

(56) References Cited

U.S. PATENT DOCUMENTS

| | | | | | |
|---|---|---|---|---|---|
| 5,664,112 | A | * | 9/1997 | Sturgeon et al. | 705/28 |
| 5,726,884 | A | * | 3/1998 | Sturgeon et al. | 705/9 |
| 5,822,745 | A | * | 10/1998 | Hekmatpour | 706/59 |
| 6,117,178 | A | * | 9/2000 | Whitney et al. | 703/12 |
| 6,292,806 | B1 | * | 9/2001 | Sandifer | 707/104.1 |
| 6,535,890 | B2 | * | 3/2003 | Sandifer | 707/104.1 |
| 6,955,100 | B1 | * | 10/2005 | Barich et al. | 73/865.8 |
| 7,031,838 | B1 | * | 4/2006 | Young et al. | 702/2 |
| 7,103,605 | B1 | * | 9/2006 | Hazi et al. | 707/102 |
| 7,171,426 | B2 | * | 1/2007 | Farmer et al. | 707/104.1 |
| 2003/0028536 | A1 | * | 2/2003 | Singh et al. | 707/10 |
| 2003/0028548 | A1 | * | 2/2003 | Nye | 707/101 |
| 2003/0187878 | A1 | * | 10/2003 | Sandifer | 707/104.1 |
| 2004/0059741 | A1 | * | 3/2004 | Whaling et al. | 707/100 |

OTHER PUBLICATIONS

Borinski et al., "Fiber Optic Sensors for Predictive Health Monitoring", IEEE, 2001, pp. 250-262.*
Frits et al., "A universal Knowledge-based Imaging System for Hazardous Environments", IEEE, 1992, pp. 211-214.*
Duda, R.O. et al, "Pattern Classification and Scene Analysis," A Wiley Interscience Publication, p. 10-39, 114-121, 130-159, 1973.

(Continued)

*Primary Examiner*—Thuy N. Pardo
(74) *Attorney, Agent, or Firm*—Howard E. Lebowitz; Foothill Law Group, LLP

(57) ABSTRACT

A computer-based method and apparatus for identifying hazardous materials based on observable physical properties and signs and systems of exposure to the hazardous materials. The observable physical properties are obtained by preprocessing plain language data to obtain normalized descriptors and modifiers pertaining to a plurality of properties and signs and symptoms. The normalized descriptors and signs and symptoms are presented to a user in lists for comparison with a sample in the field. Once a material is identified, information can be obtained from the apparatus which is necessary for response to an incident involving the hazardous material. The preferred embodiments of the invention are particularly useful to responders to a hazardous waste incident.

33 Claims, 6 Drawing Sheets

OTHER PUBLICATIONS

Frey, Peter W., Byte Magazine, Nov. 1986, p. 161-163, 165-166, 168, 170, 172, "A bit mapped classifier".

Beverly Thompson and William Thompson, "Finding Rules in Data" BYTE Magazine Nov. 1966, p. 149-152, 154, 156.

Knuth, Donald, Retrieval on Secondary Keys, Programming, vol. 3, sorting and searching (1993).

Biem, A. Katagirl, Feature extraction based on minimum classification error/generalized probabalistic descent method. IEEE International Conference on Acoustics, Speech, and Signal processing; Apr. 27-30, 1993.

Frisch, Joseph, "Bit Vectors Vitalize Data-Retrieval" Data Processing Magazines Data Dynamics, vol. 13 no. 8 pp. 37-41, Sep. 1971.

* cited by examiner

FIG. 2

Preferred Normalized Descriptors and Special Modifiers

| Color | Texture | Odor | |
|---|---|---|---|
| Amber | Chip | Alcohol | Medicinal |
| Black | Chunky | Almond | Menthol |
| Blue | Crystal | Amonia | Mothballs |
| Bronze | Fibrous | Anise | Mushrooms |
| Brown | Flake | Aromatic | Mustard |
| Copper | Fluffy | Bananas | Musty |
| Cream | Gas | Camphor | New-Mown Hay |
| Gold | Granular | Carmel | Offensive |
| Grey | Leafs | Ceder | Onions |
| Green | Liquid | Celery | Oranges |
| Orange | Metal | Chlorine | Peanuts |
| Peach | Needle | Chloroform | Pear |
| Pink | Paste | Cinnamon | Pepper |
| Purple | Plates | Cloves | Peppermint |
| Red | Powder | Coal tar | Pine Pitch |
| Silver | Solid | Coconut oil | Plum |
| Straw | Straw | Detergent | Radishes |
| Tan/Beige | Water insoluble | Disinfectant | Rancid |
| White | Water soluble | Petroleum | Rose |
| Yellow | Waxy | Fingernail Polish | Rotten eggs |
| Variable | | Fishy | Sassafras |
| Violet | | Fragrant | Sickening |
| Colorless | | Fruity | Skunk |
| Dark* | | Garlic | Spice |
| Light* | | Gasoline | Suffocating |
| Pale* | | Geranium | Sulfur |
| Bright* | | Grape | Turpentine |
| | | Honey | Vanilla |
| | Heavier than air* | Kerosene | Vinegar |
| | Lighter than air* | Lavender | Wintergreen |
| | Heavier than water* | Lemon | Bitter* |
| | Lighter than water* | Limburger Cheese | Sweet* |

\* = Special Modifiers

FIG. 3 Categorized Normalized Signs and Symptoms

Appearance
Convulsions
Cramps
Difficulty standing
Dizziness
Drooling
Drowsiness
Facial swelling
Fainting
Fatigue
Impaired reflexes
Loss of appetite
Muscle pain
Muscular stiffness
Numbness
Pallor
Paralysis
Photophobia
Ringing in the ears
Staggering
Stupor
Twitching/tremors
Unconsciousness/coma
Weak tingling arms/legs

Cardiovascular
Abnormal heart beat
Cardiac depression
Cardiac dilatation
Headache
Heart failure
Hypertension
Hypo-tension
Light-headedness
Rapid heart beat
Slow pulse
Weak pulse

Eyes
Bleeding
Blindness
Blurred vision
Burning pain
Change in color vision
Cloudiness
Dilated pupils
Dimness
Drooping eyelids
Eyelid Swelling

Respiratory
Bleeding
Bronchial inflammation
Bronchial secretion
Chest tightness/pain
Choking
Cough
Coughing up blood
Deep breathing
Difficulty breathing
Dry mouth
Fluid in lungs
Frothing of the mouth
Hoarseness
Inflamed gums
Irritation/burns
Noisy breathing
Pink frothy sputum
Rapid breathing
Respiratory arrest
Runny nose
Sneezing

Skin
Bleeding rashes
Blisters
Bluish skin
Burns
Flushed
Frostbite
Green stained skin
Inflamed skin
Irritation
Itching
Sensitivity
Spontaneous Bleeding
Stinging
Yellowed skin
———————————
Necrosis
Pinpoint pupils
Protruding eyeballs
Spasms/winking
Tearing
Unreactive pupils
Irritate/burn
Loss of coordination

Behavior
Agitation
Apprehension
Confusion
Delirium
Difficulty Speaking
Hallucinations
Hyperactivity
Lack of Concentration
Talkative

Digestive System
Almond odor urine/vomitus
Belching
Black stools
Bloody urine
Bloody vomitus
Burning pain
Coffee-ground vomit
Constipation
Defecate/urinate involuntarily
Difficulty urinating
Excessive urination
Garlic breath
Gastro. burning/irritation
Green stained tongue
Loss of feeling/lips or tongue
Metallic taste
Nausea/vomiting
Painful diarrhea
Painful urination
Red/green/brown urine
Salivation
Thirst
Watery diarrhea

Temperature
Chills
Cold extremities
Cold sweat
Fever
Sweating

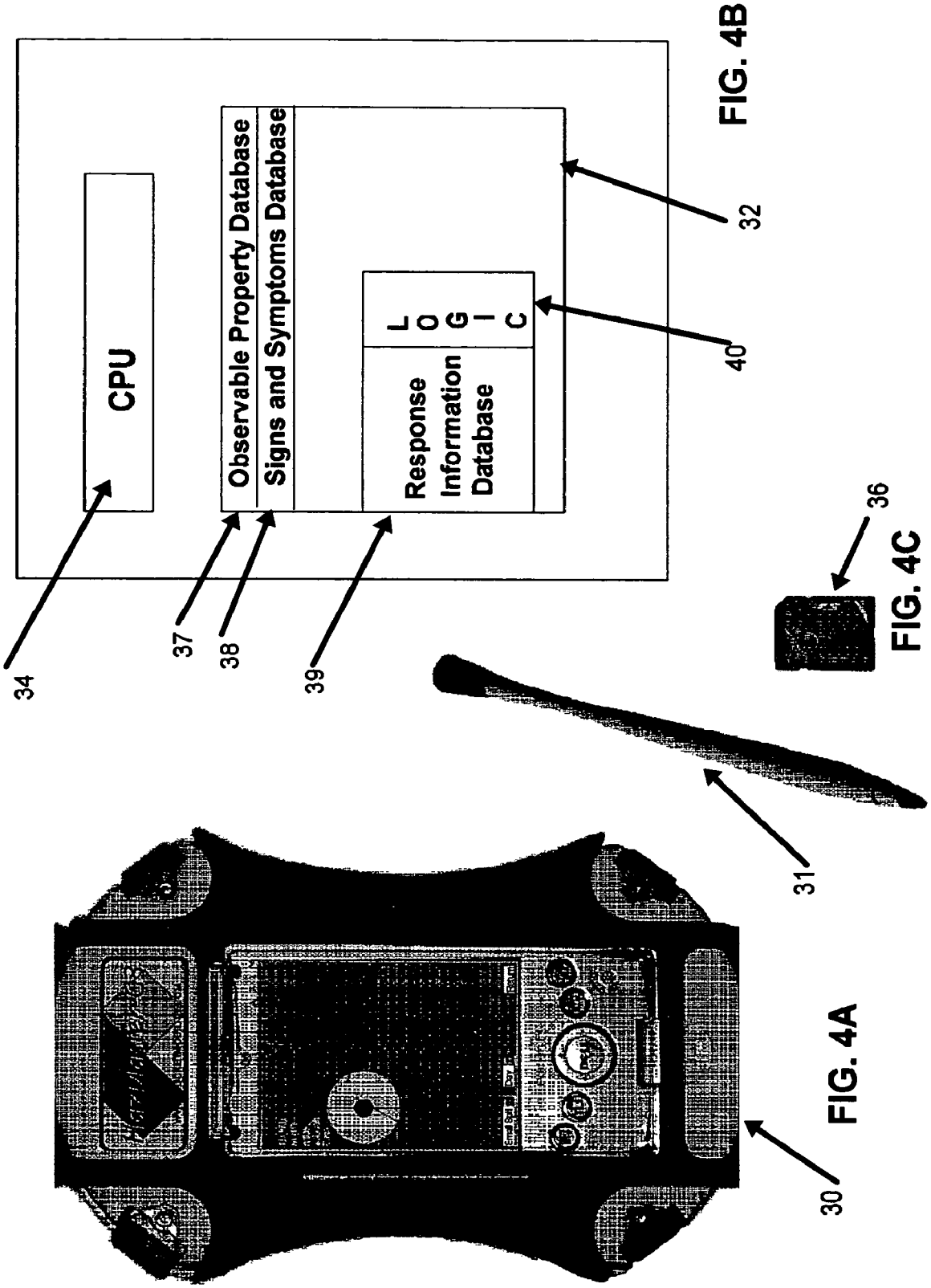

COMPUTERIZED HAZARDOUS MATERIAL RESPONSE TOOL

This application claims the benefit of my Provisional Application Ser. No. 60/469,272 filed on May 12, 2003, which is hereby incorporated herein by reference.

BACKGROUND OF THE INVENTION

1. Field of the Invention

This invention pertains to a computerized apparatus, method, and software for use in identifying hazardous materials and handling hazardous materials. The invention is particularly intended for use by responders to incidents relating to hazardous materials.

2. Description of the Prior Art

The primary problem addressed by this invention is field response to hazardous material related incidents by emergency first responders such as law enforcement personnel, fire fighters, hazardous materials forensics, terrorism response teams, and the like. In order to respond it is necessary to identify the hazardous material involved and find information and guidance needed for a safe and effective response.

The tools that are now available derive principally from authoritative documents that are provided by Federal Agencies including EPA, NOAA, DOT, NIH, NIOSH. and others. The responder's "bible" is probably the DOT Emergency Response Guide (ERG2000), which provides 62 individual response guides (orange sheets), each of which deals with a class of hazardous material that might be a single compound or individual material or a class of materials. The response guides provide safety recommendations and response information to protect the responders and the public. After securing the scene the first step in using the ERG is identifying the hazards. The ERG recommends placards, container labels, shipping documents, material safety data sheets, and rail car or trailer identification charts and provides indexes to identify the proper response guide based on these sources. It is necessary to know what a material is either by name or identifying numbers to use the ERG.

The original ERG2000 is available in document form and has been ported over to computer-based access including desktop, Pocket PC, and handheld PC platforms such as software known as Hazmatter by Pocket Mobility Inc., PEAC® by Arista Tek, Inc., and CoBRA™ by Defense Group, Inc. Some versions have added additional hazardous materials not in ERG and additional response information. Particularly, CoBRA has response materials relevant to terrorism related incidents. Like the original ERG, all of these units require a responder to learn the identity of a hazardous material either by name or identifying numbers or placards in order to reference the response information. The identification must come from external sources.

Another important reference is the EPA and NOAA chemical database that are available as the Response Information Data Sheets and is also available in a software version distributed as CAMEO® for desktop Windows and MAC computers having >50 Mb of disk space. This application is developed to supply more detailed data particular to individual hazardous materials (a single compound or product), and contains data about over 6,000 individual materials, representing over 80,000 synonyms and trade names. The CAMEO product is built on a general-purpose database manager (Filemaker™). CAMEO is designed to give first responders and planners information about properties of a spilled material and safe response. The underlying database of CAMEO is the EPA/NOAA chemical database that is the primary source of data on the physical and chemical database. While the CAMEO database manager allows text searching of the database, the database is not in a form to use the database for identifying an unknown material by observable properties. One reason is that the database doesn't use consistent language to convey the same or similar meaning. For instance, one material may be "heavier than air", while another may be "denser than air", and still another may be "more dense than air". Similarly, some materials may be "crystals", while others are "crystalline solids" or "crystalline powder". Also entering a color may refer to the color of the substance itself, its flame when burning, or the color of a decomposition product. These data are very useful for confirming a suspected identification. However, it would not be a practical way of quickly identifying an unknown material by observable properties. Notwithstanding the fact that the data is in the database, using CAMEO or another text based search of the database to identify unknown materials would be a research project rather than a tool that would be used at an emergency incident. Also, CAMEO, or other text searching with a general-purpose data base manager is too resource intensive for typical handheld computing machines in the field today, such as 16 MB RAM, using a 16 bit 20 MHz CPU.

Another approach involves various chemical analytical tools that might be useful for chemical analysis, such as ionizing spectrometers, infrared fast Fourier Transforms, mass spectrometry, and the like. These are useful devices but require specialized technicians that are often not available on first response, but are more practical at a later stage of the response.

What is needed is a computer-based apparatus for identification of hazardous materials by responders to a hazardous waste incident based on readily observable properties of the hazardous material.

There is a further need for a computer-based apparatus for providing response information needed by responders to a hazardous materials incident, such information specific to a hazardous material that was identified based on its observable properties.

There is a further need for a computer-based apparatus useful in identifying a hazardous material by signs and symptoms associated with exposure to the hazardous material.

There is a further need for a computer-based apparatus useful for identifying a hazardous material based on observable properties and signs and symptoms of exposure, and also providing response information needed by responders to a hazardous material related incident in a single apparatus which can be provided as software operable on a variety of general use computer platforms including limited performance palm-top devices such as PDAs and smart cell phones and the like as well as laptop and desktop computers.

SUMMARY OF THE INVENTION

It is an object of the invention to provide a computer-based apparatus for use in identifying hazardous materials based on readily observable properties of the hazardous material suitable for use by responders to a hazardous materials incident.

It is a further object of the invention to provide a computer-based apparatus for providing response information needed by responders to a hazardous materials incident, such information specific to a hazardous material that was identified based on its observable properties.

It is a further object of the invention to provide a computer-based apparatus useful in identifying a hazardous material by signs and symptoms associated with exposure to the hazardous material.

It is a further object of the invention to provide a computer-based apparatus for use in identifying a hazardous material based on observable properties and also providing response information needed by responders to a hazardous material related incident in a single apparatus which can be provided in a hand-held computer platform.

It is a still further object of the invention to provide a computer-based apparatus useful for identifying a hazardous material based on observable properties and signs and symptoms of exposure, and also providing response information needed by responders to a hazardous material related incident in a single apparatus which can be provided as software operable on a variety of general use computer platforms including limited performance palm-top devices, such as PDAs and smart cell phones and the like, as well as laptop and desktop computers.

It is finally a further object of the invention to provide a computer-based apparatus for use in identifying hazardous materials by first responders without scientific or technical training using a palm top or portable computer programmed for identifying the material based on readily observable properties and common language descriptors.

A first aspect of the invention is a method for preprocessing hazardous material descriptions to render them useful for subsequent identification of hazardous materials based on hazardous materials processing. There are several standard references that provide data on properties of hazardous materials, such as the chemical database in The Environmental Protection Agency's CAMEO database (formerly Response Information Data Sheets). Other sources for properties are the USAMRID for biological warfare agents. The raw data in these references might be somewhat useful for verifying a suspected identification, but it is not in a form that is readily useful for identifying an unknown hazardous material. There are over 6,000 discreet materials in the CAMEO database alone representing over 80,000 common and trade names. The plain language descriptions of the materials (such as color or texture of the material) are commingled with other properties using the same words. For instance, mention of a color might refer to the color of the material itself, to the color of the flame when the material is burned, or to the color of a decomposition product. Also, synonyms are frequently found and different phrases are used with similar meanings. For instance, one material may be "heavier than air", while another may be "denser than air", and still another may be "more dense than air". Similarly, some materials may be "crystals", while others are "crystalline solids" or "crystalline powder". These factors would make word searches of the databases difficult to use for identification of an unknown hazardous material even if a sophisticated database manager was available with a skilled user. The data must be preprocessed into useful information, and put into a format from which a user can select the relevant properties he observes in the field. A method according to the invention is described in the steps that follow:

1. contextually parsing plain language descriptions of the hazardous materials to identify a list of relevant descriptors and a plurality of modifiers pertaining to observable properties of the hazardous materials.
2. classifying and organizing the descriptors and modifiers into a plurality of property groups each of which describe a property of a hazardous material. In the preferred embodiment of the invention, the properties chosen are color, texture, and odor.
3. normalizing the list of descriptors and modifiers by replacing synonymous words and phrases with consistent normalized wording.
4. assigning unique binary values to each descriptor and each modifier in each property group, such that one binary value represents that the descriptor or modifier is "present" in the description of a particular hazardous material, and the other binary value indicates that the descriptor or modifier is absent in the description of the material. Preferably the "present" value is 1, and the "absent" value is 0. When this step is completed there are a plurality of property groups (three in the preferred example) each of which is a sequence of bits in which each bit represents either one descriptor or one modifier or is unassigned. A full record comprises one of each of the plurality of descriptor groups in a predetermined order and represents a full description of one hazardous material. Also, within each property group the modifiers are grouped together at one end of the bit sequence of that group.
5. compiling together a computer usable file comprising a sequence of records, such that each record represents one hazardous material. In the preferred embodiment, the number of bits in each property group, is equal to or evenly divisible into a natural word size of a computer on which the data will be used. In the preferred example, color and texture have 32 bits each and odor has 64 bits, so a fixed length record has 128 bits.

Another aspect of the invention is a computerized method for identifying a hazardous material. The method, implemented in software operating a general purpose computer, is preferably intended to run well on a minimal capability handheld or palm computer, typically 16 MB, and a CPU of 20 MHz, and 16 bit CPU, having an input device, an output device, a CPU, and computer memory. It will of course also operate on more capable laptop or desktop computers. The invention could also be implemented in firmware, in whole or in part, and could be made as a single purpose computing device. The method is comprised of the steps that follow.

1. storing a first database in the computer memory. Each record represents a hazardous material and comprises of a bit sequence wherein each bit can be assigned either a "present" value or an "absent" value wherein each bit is either a normalized descriptor of an observable property of a hazardous material, a special modifier, or an unassigned position. Preferably the "present" value is 1, and the "absent" value is 0. In a preferred embodiment the first database is a sequential list of fixed length records, such as previously described in the first aspect of the invention wherein record has a relative position in the sequential list.
2. storing a computer representation in the computer memory, of response information relevant to use with the hazardous materials represented in the first sequential list. These include such information as EPA Response Information Data Sheets (RIDS), the Department of Transportation Emergency Response Guides (ERG2000), and the NIOSH Pocket Guides. These response information are compressed and stored for access according to the sequential position of the hazardous material to which they pertain or random access. The storage is preferably such as to allow display of the data in a format and organization on screen that is similar to the original source.

3. displaying property lists on the computer output device, preferably the screen, of the type from which a user can make selections, wherein each property list pertains to one of the observable properties of hazardous materials in the sequential list. The choices are either normalized descriptors of the observable property or special modifiers pertaining to the observable property. The preferred format for display is pop up menus.
4. accepting one or more selections from a user from one or more of the property lists and storing the user defined selections in computer memory in a format compatible with comparison with a record in the sequential list. As described in the first aspect of the invention, in the preferred embodiment, the fixed length records each consist of an ordered sequence of property groups, each property group is an ordered sequence of bits, each bit represents the presence or absence of a descriptor or modifier or is unassigned, and within a property group the modifiers are grouped together, and the presence of modifiers is optional. The property groups in the fixed length records correspond to the property lists displayed, and the descriptors and modifiers on the property list correspond to descriptor and modifier bits in property groups. The user-defined selections from each property list are preferably stored in a bit sequence with the same sequence as the corresponding property group in the fixed length records. If a particular property group includes modifiers as well as descriptors, a user defined selection will consist of a user defined descriptor bit map and a user-defined modifier bitmap.
5. comparing the user selection with a fixed length record representing a hazardous material. This step comprises making at least one bit wise logical comparison between a user defined selection and fixed length record. Many possible criteria for a match will be apparent, however it has been found that one preferred method is of particular value. Based on trials, the preferred criteria is to consider a material a potential match to a user selection if for each descriptor group in the fixed length record that corresponds to a property list from which at least one selection was made, there is at least one bit with "present" value that corresponds to a selected bit, if any, in the user defined descriptor bitmap, and that there is at least one bit with the "present" value that corresponds to a selected bit, if any, in the user defined modifier bitmap. This step can be implemented by making two bitwise AND operations for each property list from which one or more selections were made. For either a 16 bit or 32 bit CPU and a 32 bit descriptor list this is a very search efficient operation, which is important for low performance hand held computers. This step is repeated for each hazardous material record in the sequential list and a list of possibly matching materials is reported to the user on the display device.
6. allowing a user to highlight a possible hazardous material and select relevant information on response to an incident involving the highlighted hazardous materials. The data are extracted from the computer representation of relevant response information and are displayed in a manner similar to the original government documents from which the data was extracted.

Having both comprehensive identification and response information for hazardous materials on a single palm held computational device is believed to be unique to this application.

An optional and very useful feature of the method is identification of a hazardous material by signs and symptoms of exposure to the hazardous material. In the case of signs and symptoms the acts of parsing, classifying, normalizing, assigning and compiling are carried out very much as in the first aspect of the invention for observable properties. However, it has been found that the frequency of occurrence of different signs and symptoms is very skewed, skewed such that about 20% of the signs and symptoms are responsible for 80% of the occurrences. The performance on a relatively low performance computer can therefore be dramatically improved by listing the bits in a record by order of occurrence. There are no modifiers for signs and symptoms. A preferred method is compiling a list of sequential records for signs and symptoms with the bits in each record arranged by descending order of frequency of occurrence, and to report the materials with the highest rank, where rank is the number of matching bits between the user selection and a sign/symptom record. The evaluation is carried out by examining the records one word (32 bits) at a time such that in most cases it will not be necessary to go beyond the first word of each record. In the preferred embodiment there are 128 bits per record. The sign/symptom sequential list, the sequential list of records representing physical properties, and the computer representation of response information are preferably all in memory concurrently.

BRIEF DESCRIPTION OF THE DRAWINGS

These and other features, aspects and advantages of the present invention will become better understood with regard to the following description, appended claims and accompanying drawings, where:

FIG. 2 is a table of preferred values of normalized descriptors and special modifiers in the database of FIG. 1.

FIG. 3 is a table of preferred values of classified signs and symptoms.

FIG. 4A is a drawing of a computer suitable for practicing the invention.

FIG. 4B is a schematic of the computer.

FIG. 4C is a memory card with software instructions and data files for carrying out the invention.

DESCRIPTION OF THE PREFERRED EMBODIMENTS

Figure 1:
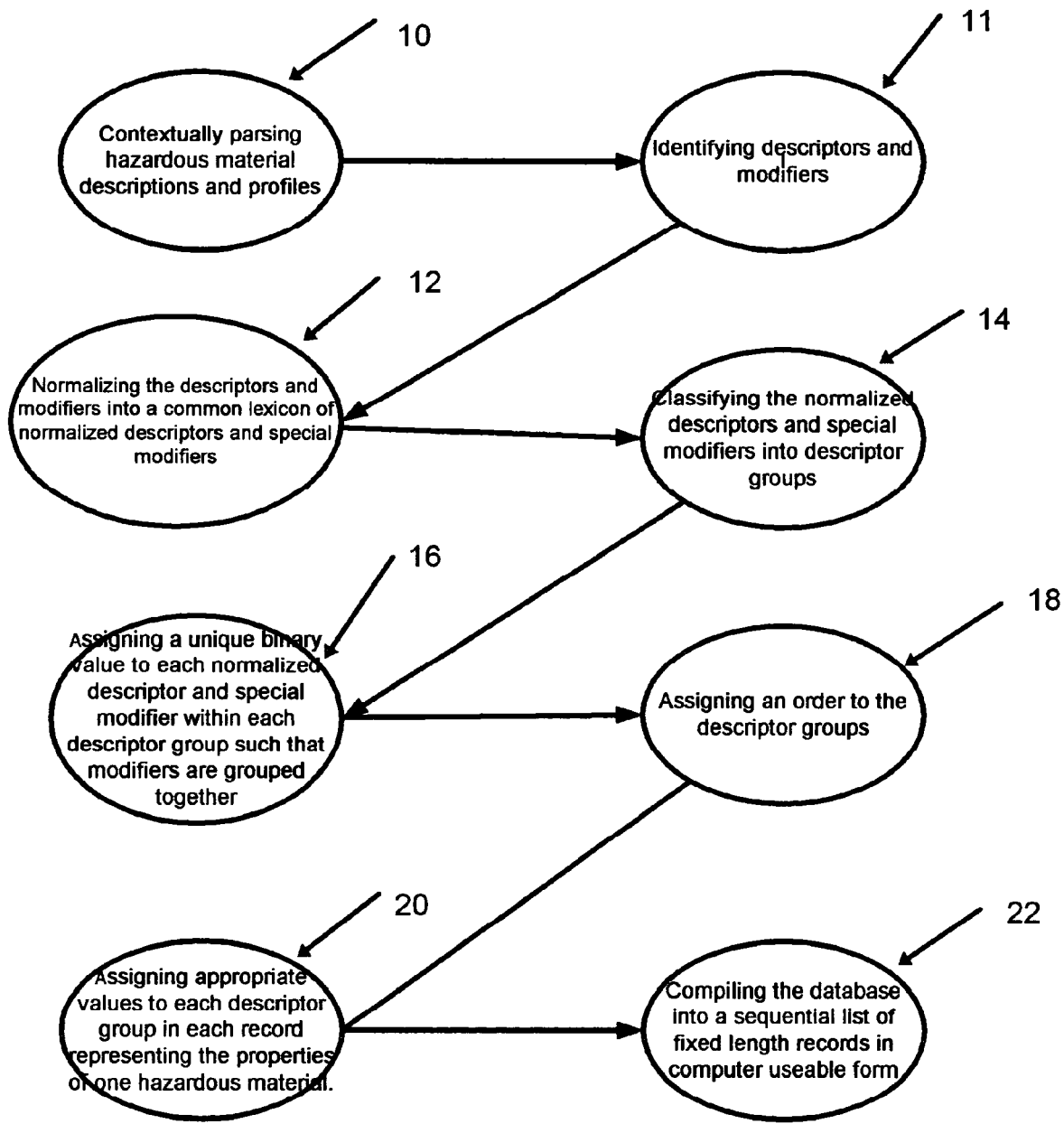
FIG. 1 is a flow chart of the method of making a database for use in a computerized tool for identifying hazardous materials according to a preferred embodiment of the invention.

The invention involves a computerized tool for use in connection with hazardous materials related incidents. While it will be apparent to those skilled in the art that the invention has a variety of uses, an intended use is for responders to a hazardous materials incident, such as police, fire, emergency medical personnel, hazmat teams, and the like.

One aspect of the invention is a hazardous material property database, and a method of making the database for maximum utility for field identification of hazardous materials by responders to hazardous waste incidents, preferably first responders. Another aspect of the invention is a computer including data and software instructions in computer memory that allows a user to identify a hazardous material based on observable physical properties, by choosing descriptors and modifiers of a physical property from prepared lists of normalized descriptors and modifiers. Preferably, the user may obtain response information by marking a hazardous material and selecting the desired type of data. Another aspect of the invention is a method of identifying hazardous materials in the form of computer instructions and data files in computer useable form which when loaded and executed will operate on a general purpose computer. A preferred platform is a hand held or palm top PDA device having less than 16 MB of memory and about 9.8 MB of free memory, and the invention should be capable of operation on such a machine. Such a palm held machine 30 is shown in FIG. 4A. FIG. 4B shows the memory 32 and processor 34 in the machine. In the memory is shown the observable properties database 37, and the signs and symptoms database 38, both of which are composed of sequential records in the preferred embodiment. Also shown are the response information database 39 and the computer program logic 40 in memory. FIG. 4C shows a memory card 36 with computer programming instructions and data in a computer useable form for carrying out the invention. It will be understood to those skilled in the art that computer useable form can also include any format appropriate for the computer, including but not limited to all manner of disks and including transferring files and data over a network, by direct connection, or by IR or radio signals.

Important features of a preferred embodiment of the invention implemented on a portable handheld PDA include:

1. ability to identify a hazardous material based on making selections from pre-prepared lists of including both normalized descriptors and modifiers relevant to observable properties. The normalized descriptors and modifiers are derived by contextually parsing plain language descriptors and profiles of hazardous materials to identify relevant descriptors and modifiers and normalizing these to a common lexicon.
2. ability to identify a hazardous material based on making selections from pre-prepared lists of normalized signs and symptoms of exposure to hazardous materials.
3. ability to reference response information needed by a responder to a hazardous materials incident relevant to an identified hazardous material.
4. data structures and computer logic for storing databases, facilitating user inputs, and efficiently identifying hazardous materials from the user inputs.

The invention will now be described in terms of several databases that may be included in the invention and how to make them, and the computer logic and resources to carry out the invention.

Databases

Database of Observable Properties and Method of Making the Database

One component of the invention is a database of observable properties of hazardous materials organized into a sequential list of fixed length records for use in a computerized tool for identifying hazardous materials. The database format is specially chosen for use in the field identification of hazardous materials in the following ways:

1. The plain language profiles and descriptions of thousands of hazardous materials found in government references are pre-processed into property groups of normalized descriptors and special modifiers to facilitate their use in identification of hazardous materials. As used in this patent application a "normalized descriptor" is defined as an attribute of an observable property of a hazardous material, that has been obtained by the steps of contextually parsing a multiplicity of hazardous material profiles to identify attributes, grouping the attributes into property groups, identifying synonymous and similar words and phrases and replacing them with a single standardized term which is used consistently throughout the database. Similarly, "special modifiers" is defined as a word which can under some circumstances describe an attribute of an observable property of a hazardous material and under other circumstances describe a hazardous material. For instance for the observable property color, normalized descriptors might be red, orange, yellow, green, blue, and colorless, while special modifiers might be dark, light, pale, and bright. The data are stored in a compact data structure to where the presence or absence of each descriptor or special modifier in the description of a hazardous material is represented by the value of a single bit (this is equivalent to each descriptor or modifier being assigned a distinct value that is a power of two).
2. The data are grouped into property groups which have a number of bits which is preferably a natural word size of the system (32 bits) so that a selection made by a user can be evaluated against 32 properties with a single bitwise logical comparison. This improves performance substantially on low performance machines.
3. All of the above factors, convert data into information to be efficiently searched without use of a general purpose database manager, the use of which would prohibit use on low performance hand held devices.

Each fixed length record represents the properties of one hazardous material and has a relative position in the sequential list. Each fixed length record consists of a bit sequence where each bit either represents a normalized descriptor of an observable property, a special modifier, or an unassigned space. Each normalized descriptor and each special modifier is represented in the bit sequence as one bit that can have either a "present" value or an "absent" value, preferably the "present" value is 1 and the "absent" value is 0. Each record has the same order as to which position represents a particular normalized descriptor, special modifier, or unassigned space. Each record is preferably divided into a plurality of property groups. Each property group is comprised of normalized descriptors relating to the property groups and optionally special modifiers. In the preferred embodiment, the property groups are color, texture, and odor. Examples of normalized descriptors of color are red, orange, yellow, green, blue, and colorless; examples of special modifiers are dark, light, pale and bright. Note that special modifiers preferably make sense as either a modifier of a normalized descriptor or as a stand-alone word. For instance, it makes sense to have a dark blue material or just a dark material. A preferred list of normalized descriptors and special modifiers is given in FIG. 2. The data base is manufactured onto a computer useable form such as but not limited to a memory card such as the card 36 in FIG. 4C, for use in a palm top computer, or a file for upload to a computer, or other manufactures that will be well known to those skilled in the art.

The method of making the database for use in identification of hazardous materials is now discussed. The descriptions and profiles of hazardous materials are not organized for use in rapid field identifications. They are rather intended for use in finding properties of a known material not for identifying an unknown material. FIG. 1 is a flow chart of a preferred embodiment of a process for compiling a database for use in the invention. The steps are as follows:

1. Using a comprehensive group of hazardous materials from references such as the EPA/NOAA CAMEO database of over 6,000 hazardous materials, contextually parse the plain language descriptions of the multiplicity of hazardous materials to identify a plurality of relevant descriptors and a plurality of modifiers pertaining to observable properties of the of hazardous materials (10 and 11). Those skilled in the art will appreciate that other sources may be available or become available to supplement or replace the suggested references.
2. Normalize the plurality of descriptors and plurality of modifiers into a common lexicon of normalized descriptors and special modifiers by replacing synonyms and similar phrases with normalized wording (12).
3. Classify each normalized descriptor and each special modifier into one of a plurality of descriptor groups, wherein at least one of the descriptor groups preferably comprises a plurality of special modifiers. Each descriptor group represents an observable property. In a preferred embodiment, the descriptor groups are color, texture, and odor. The normalized descriptors and special modifiers in the preferred embodiment are listed in FIG. 2 (14).
4. Assign a binary power of 2 to each normalized descriptor and to each special modifier in each descriptor group, such that each normalized descriptor and each special modifier in each descriptor group is represented by exactly one bit and such that the modifiers are grouped together within each descriptor group. Since there will be more descriptors than modifiers it is convenient to assign the modifiers the lowest values in each descriptor groups, so that each descriptor group that contains one or more modifiers is a bitmap consisting of a descriptor portion and a modifier portion. In using the database to identify a hazardous material by comparing a user made selection with a record in the database, bits representing normalized descriptors and special modifiers will be treated separately (16)
5. Assign an order to each of the plurality of descriptor groups, such that each fixed length record consists of a sequence of descriptor groups in the order. For instance, in the preferred embodiment the order is color, texture, and odor (18).
6. Assign appropriate values to each descriptor group in each fixed length record that represents a hazardous material, such that the sequence of descriptor groups describes the hazardous material. This is accomplished by assigning each descriptor bit and each modifier bit as being present or absent in each descriptor group of a record according to whether it is present or absent in the description of the hazardous material that the record represents (20).
7. Compile the database into a sequential list of fixed length records in computer useable form (22).

Optional Signs and Symptoms Database

An optional feature in identification of hazardous materials is the ability to identify a hazardous material by signs and symptoms of exposure to the hazardous material. This may be very useful to a first responder who arrives at the scene of an incident and finds victims in distress from exposure to a hazardous material. As with the database of observable properties, the signs and symptoms data are preferably organized as a sequential list of fixed length records with each bit in the record representing the presence or absence of one normalized sign or a symptom of exposure, or an unassigned space.

The signs and symptoms database is compiled in a manner similar to the properties database. The database is compiled by the following acts:

1. Gather signs and symptoms for exposure to those hazardous materials for which it is available. Sources include the EPA Response Information Data Sheets, National Institutes of Health National Toxicity Program Database, and the ATSDR database, preferably in their latest editions or revisions. Those skilled in the art will appreciate that over time new sources may become available to supplement or replace the listed items. The signs/symptoms database has fewer materials listed than the observable properties database; not every hazardous material in the properties database has available signs and symptoms of exposure.
2. Normalize signs and symptoms into a common format by eliminating synonyms and preferably using common language rather than medical terminology. For instance, tearing can be used to replace lacrimation, watery eyes, causes tears, watering eyes, tearing eyes, etc.
3. Classify the normalized signs and symptoms into categories. There are eight categories in the preferred embodiment, including appearance, respiratory, behavior, cardiovascular, skin, digestive system, eyes, and temperature. There are 128 signs and symptoms in the preferred embodiment. A table of the classified signs and symptoms is given in FIG. 3
4. Assign a binary power of two to each sign and symptom, so that each bit in the record represents the presence or absence of one sign or symptom. Unlike the properties database, signs and symptoms are preferably listed in order of frequency of occurrence rather than by category group. This is because of the fact that the signs/symptoms data are very skewed, with about 20% of the signs or symptoms accounting for 80% of the occurrences. If it is desired to quickly search the data for the most likely hazardous materials corresponding to observed symptoms, a much more efficient search will be facilitated if the signs and symptoms are arranged in order of frequency of occurrence.
5. Assign an appropriate value to each bit in each record corresponding to a hazardous material depending on whether the assigned sign or symptom is present or absent.
6. Compile the database into a sequential list of fixed length records in computer useable form.

Response Information Database

Once a hazardous material has been identified, it is preferable to be able to display response information that a responder will need to handle an incident involving the hazardous material. The information includes:

1. Name, synonyms, United Nations Number (UNNA), Chemical Abstract Service Number (CAS)
2. Emergency Response Guidebook (ERG2000)—This is a guidebook that was prepared by the US Department of Transportation, Transport Canada, and the Secretariat of Communication and Transportation of Mexico. The guidebook contains 62 individual guides (orange sheets) with safety and emergency response information for a class of hazardous materials and indexes for choosing the appropriate index for a particular hazardous material based on name or identification number.
3. EPA/NOAA Response Information Data Sheets (now found in CAMEO).

4. Hazards Overview—Including airborne concentration immediately dangerous to life and health (IDLH) from NIOSH, EPA and NIH sources, temporary emergency exposure levels (TEEL), shipping hazard, water hazard, other hazards.
5. Chemical Profile—Text
6. Reactive Groups—Text
7. Physical Properties such as auto ignition, boiling point, ERPG1, ERPG2, ERPG3 (ERPGx values are maximum allowable air concentration for x hour exposure without harm), flash point, lower explosive limit, upper explosive limit, melting point, specific gravity, temporary emergency exposure limits (1, 2, and 3 hours), vapor pressure, vapor density, ionization potential, and correction factors
8. Emergency Medical Service—signs and symptoms, first aid,
9. Protective Clothing—permeation threshold times for various materials and types of clothing
10. National Fire Protection Association (NFPA) placard.

The response information is reduced to compressed form such that can be accessed for any chosen hazardous material discovered in a property search, signs and symptoms search (if applicable) or search by name, synonym, UNNA or CAS Number. The compression of data is important to the operation on portable computers, such as hand held or palm top computers, since some of the references are large text documents.

The original reference for each material is the relative position of the corresponding record in the Observable Properties Database. This links to a master record for every material in the system. The master record allows the program to quickly present an overview of any material found in the system. Also, the data found in a master record can be used as keys into the rest of the data, allowing retrieval of more detailed data whenever the user requests an appropriate detailed data page.

One particularly large document that is preferably available in memory is the Emergency Response Guidebook (ERG2000). The data records for the ERG source alone are 1.58 MB as supplied without display or formatting instructions. An Acrobat version of ERG2000 is 1.75 MB and 383 pages. The preferred method of storing the ERG is a Hoffman coding technique of storing an alphabetically sorted list of each unique sentence in the document (there is substantial reuse of sentences), along with indexes and other data needed to re-create the source data in about 234 KB. The methods of indexing and linking to particular materials are conventional and well known to computer programmers.

Another area of the data requiring special treatment is providing guidance on chemical protective clothing (whether and how long a particular material of construction can be counted on to provide protection for a particular hazardous material). Chemical protective clothing source data comes primarily from the NIOSH Pocket Guide, the EPA's RIDS database, and 3M Corporation's Guide to Permeation, which provides extensive data regarding their line of chemical protective clothing materials, which constitutes approximately 70% of all chemical protective clothing/materials. Data sources are provided with different precision in different sources. As this system is intended primarily as a field guide for first responders, the data are normalized into broad categories that will be useful for the intended purpose and also reduce the amount of data required to load into memory. For instance, a fireman doesn't need permeation times broken down by the minute even though that information may be available. The permeation breakthrough data is stored and available for presentation based on twelve categories (stored as 12 bits) based on the following categories: No data, <1 hour, 1-3 hours, at least 3 hours, <1 hour (limited data), 1-3 hours (limited data), at least 3 hours (limited data), at least 4 hours, at least 5 hours, at least 6 hours, at least 8 hours, and at least 12 hours. A given chemical may have numerous types of chemical protective clothing, in the categories of garments, gloves, boots, similar fabrics and face-shields. The sequence number in the Observable Property Database correlates each to a material. By this manner of data compression the permeation breakthrough data is reduced from 1 MB to about 68 KB.

Text data such as first aid information, signs and symptoms information, are available in the literature as free text data from multiple sources. The text as supplied is preferably pre-processed and normalized into a set of single line sentences that express all the instructions in the original sources. The normalized sentences are stored in memory along with indexes to create the original instructions for each hazardous material. Physical properties are preferably sorted to identify all the unique values of a given property, and then store indexes to lookup the proper data.

The NFPA hazard code is compressed into one 16 bit word for each material.

Computer Logic

A preferred language for implementation is Java using the Superwaba platform that is an open source platform for PDA applications development available on the Internet at "www-.superwaba.com.br". This platform has a Virtual Machine implemented for windows, Palm OS, Pocket PC (Windows CE), and Symbian devices.

The computer logic follows the event driven model, where the events are initiated by user inputs. In a preferred embodiment implemented on a handheld PDA user inputs are generally made by a stylus and touch sensitive screen, and output is shown on the screen. This is probably the most convenient platform for an emergency responder and it is an important consideration that the invention be capable of operation on such familiar handheld units as a Palm OS 3.0 or higher, Microsoft Pocket PC 2002, 2000, HPC211 or PPC211 device based on ARM, MIPS, or SH3 processor with 9.8 MB main memory free. Of course, it will also operate on Windows NT, ME, 2000, XP, or 98 with at least 9.8 MB free disk space, or Linux, Unix or Macintosh computers with an installed Java Runtime Environment (JRE) 1.3 or higher.

Figure 5A:
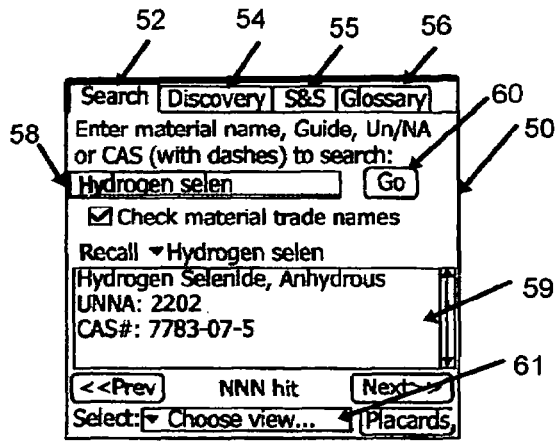
FIG. 5A is a screen shot of the search mode of a preferred embodiment of the invention on startup.
Figure 5B:
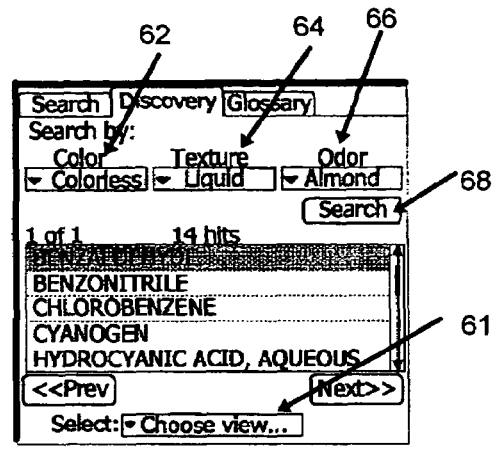
FIG. 5B is a screen shot of the materials identification page.
Figure 5C:
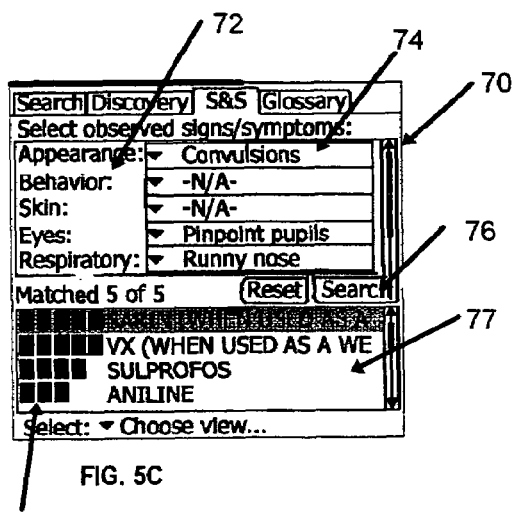
FIG. 5C is a screen shot of a signs and symptoms identification page.
Figure 5D:
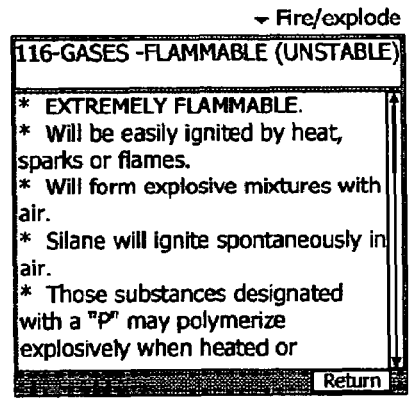
FIG. 5D is a screen shot of an Emergency Response Guide Orange Sheet.
Figure 5E:
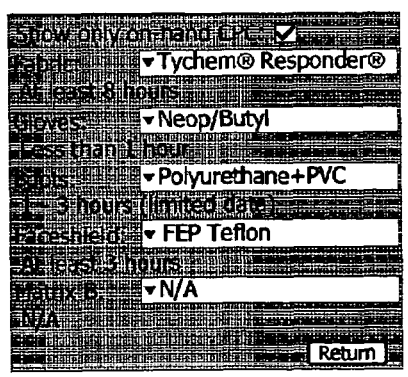
FIG. 5E is a screen shot showing recommended protection equipment.

FIG. 5A shows an opening screen 50, for the invention. Note three tabs labeled Search 52, Discovery 54, S&S 55 (Signs and Symptoms) and Glossary 56, with the Search tab 52 chosen as the opening screen. From this screen one can search for a hazardous material by entering its name or part of its name into input box 58 and pressing GO 60. An ERG Guide Number, a Guide section, a United Nations number (UNNA) or a Chemical Abstract Service (CAS) number may be inputted in place of the name. The result is reported to results box 59. In search mode a user may select available data for a material by tapping the choose view menu 61. This brings up a pop-up menu of response information that is available for this material, such as the relevant Emergency Response Guide page, isolation distance, hazards review, reactive groups, material profile, protective clothing, EMS signs and symptoms, and first aid. Tapping the appropriate item causes the computer logic to retrieve the appropriate information from the Response Information Database and assemble it on the output screen. FIG. 5D shows a screen shot of an ERG page and FIG. 5E shows a page with recommendations of chemical protective clothing.

A user may shift to discovery mode from this screen by tapping Discovery tab 54 in FIG. 5A. In discovery mode a user is able to identify a hazardous material by observable properties, a capability that is a key innovation unique to this invention. FIG. 5B shows the discovery mode input page, with pop up menus for a user to input properties of color 62, texture 64, and odor 66. By tapping any one of these menus a list of descriptors and modifiers pops up for selection. The descriptors and modifiers for each property in a preferred embodiment are shown in FIG. 2. These same descriptors and modifiers correspond one to one with the descriptor groups in the database of observable properties. A user can make as many choices from each list as she desires. When satisfied with her choices the user should tap the search icon 68. This causes the computer logic to form a user-defined bitmap for each list from which at least one selection was made and store the user-defined list in memory. The user-defined bitmap for a list preferably has the same structure as the corresponding descriptor group in the database of observable properties and places the "present" value in the position of each user selection and the "absent" value in all of the other bit positions. Recall that some descriptor groups in the database include both descriptors and modifiers, and if so, the modifiers are grouped together so that these descriptor groups consist of a descriptor portion and a modifier portion. The same convention is preferably followed in the user-defined bitmap. The computer logic then compares each user-defined bitmap with each record in the database of observable properties to see if it matches according to a matching criterion.

Those skilled in the art will appreciate that there are many ways to judge whether a user selection is a "good enough" match to a record in the database of observable properties to report a hazardous material as a potential match for an observed material. The observable property database is set up with each bit in a descriptor group, which is assigned, representing either a normalized descriptor or a special modifier, and the user-defined selection from a property list which corresponds to the descriptor group has the same bitwise structure as the descriptor group. Therefore, a preferred method of comparing a user-defined selection and a descriptor group is the bitwise logical AND. For a first bit stream and a second bit stream, each bit stream having the same number of bits, and each bit having a position, the bitwise logical AND of the two bit streams returns a 1 for each bit position where a 1 in the first bit stream is matched by a 1 in the second bit stream and returns zero otherwise. For example, 0111 AND 0001 equals 0001.

While many criteria are possible, the preferred criterion is an inclusive method that will return excess potential matches at the expense of not excluding the correct choice. This method was found to be most useful in testing by first responders. Preferred methods therefore should not require that all properties of a material in the database be matched by user observation.

The preferred method considers a sample material to be a potential match of hazardous material represented by a record in the database if for each descriptor group in the record that corresponds to a property list from which at least one selection was made, there is at least one bit having the "present" value that corresponds to a selected bit, if any, in the descriptor portion of user-defined bitmap, and that there is at least one bit having the "present" value that corresponds to a selected bit, if any, in the modifier portion of the user-defined modifier bitmap. In the preferred embodiment where the "present" value is 1 and the "absent" value is 0, for each descriptor group in the record that corresponds to a property list from which at least one selection was made and therefore having a user-defined bitmap, the logical bitwise AND is non-zero 1. between the descriptor portion of the user-defined bitmap and the descriptor portion of the corresponding descriptor group in the record, if a descriptor was selected from the property list, and
2. between the modifier portion of the user-defined bitmap and the modifier portion of the corresponding descriptor group, if a special modifier was selected from the property list.

Figure 6:
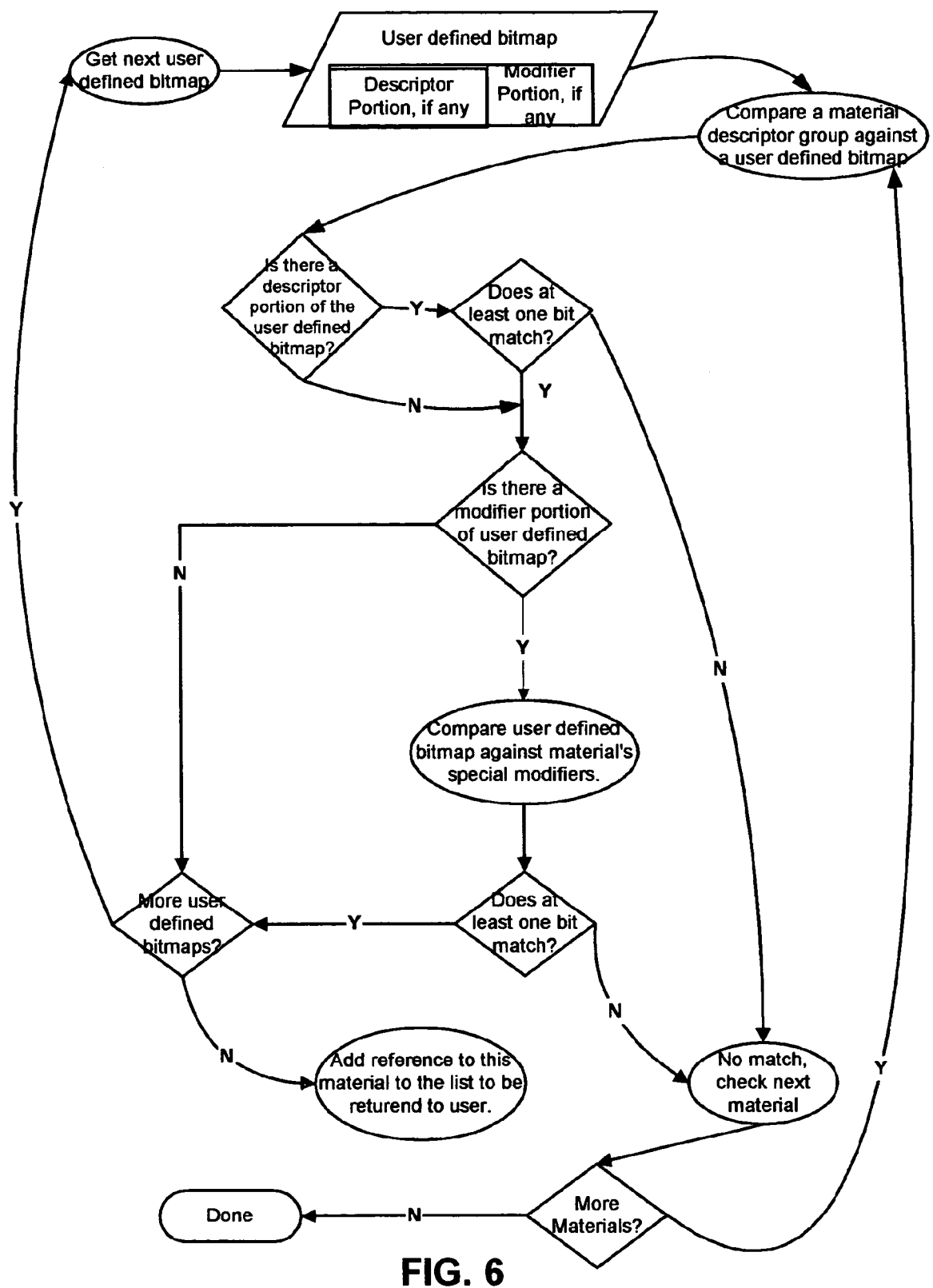
FIG. 6 is a flow sheet for processing data to identify potential hazardous materials.

This process is repeated for each hazardous material in the observable properties database and the potentially matching hazardous materials are reported to the user on the output screen. FIG. 6 is a flow diagram of the method of comparison.

One interesting property of the preferred matching criterion is that if only a modifier and no descriptors are chosen from a property list, the modifier will in effect serve as a descriptor. For instance, in the color property list if only "dark" is chosen, any dark material will be a match (recall that a "dark" material will have the "present" value in the "dark" bit position). Also, if both descriptors and modifiers are selected, there must be at least one match between in both the descriptor and modifier portions.

Once a list of potentially matching hazardous materials is presented to a user, the user can enter the select choose view icon 61 which makes available a pop-up menu of information available on a hazardous material selected from the list. The information includes information to further assist in narrowing the identity of a hazardous material sample, as well as response information. The information includes items such as the relevant Emergency Response Guide page, isolation distance, hazards review, reactive groups, material profile, protective clothing, EMS signs and symptoms, and first aid. Tapping the appropriate item causes the computer logic to retrieve the appropriate information from the Response Information Database and assemble it on the output screen. For example, FIG. 5D shows a screen shot of an ERG page and FIG. 5E shows a page with recommendations of chemical protective clothing.

Another very useful feature is to search for a hazardous material by signs and symptoms of exposure to the material. The event by which a user activates a search by signs and symptoms on a palm top embodiment of the invention is tapping the S&S tab (55) on the opening screen illustrated in FIG. 5A. This brings up a screen 70 illustrated in FIG. 5C which lists eight categories of signs and symptoms 72 (five visible in the figure, the remaining three would be viewed by scrolling down the list) next to pop up menus 74 for entering individual indicators (signs or symptoms) in each category. The categories and indicators are listed in FIG. 3. As many signs and symptoms could be selected as desired from each category. When the selection process is complete, the search event is initiated by a user tapping the search button 76. This begins the computer logic to begin the search.

As was previously described in the section entitled "Optional Signs and Symptoms Database" a slightly different data structure is preferred for signs and symptoms. Like the observable properties database, the preferred structure is a sequence of fixed length records, one record for each hazardous material, where each bit represents the presence or absence of one indicator or an unassigned space. In the preferred embodiment each record is 128 bits long, and a present indicator is represented by the bit 1 and an absent indicator is represented by the bit 0. Unlike the observable properties database, in the signs and symptoms data base the bits (representing indicators) are preferably not arranged within a record in groups corresponding to the categories presented to a user to make selections, but are rather arranged by frequency of occurrence. As a consequence the correspondence between bit position and indicator must be stored in a look up table. Using records arranged by frequency of occurrence allows a search strategy that exploits the observation that the occurrence of the indicators is quite skewed, with about 80% of the occurrences resulting from only 20% of the indicators.

In the case of signs and symptoms it is therefore preferred to present the hazardous materials in rank order, the rank of a material preferably being equal to the number of user inputted indicators which are present in the material. The top ranking 25 materials are reported in the preferred embodiment. Ranking the materials replaces the comparison criteria used in identifying by observable properties. The computer logic preferably comprises the following steps:

1. Assembling a user defined indicator bitmap in the same format as the record bitmap stored in the signs and symptoms database.
2. Examining each record, in turn, in the database by examining the first word in the record by computing a bitwise logical AND between the first word of the record and the first word of the user defined indicator bitmap and computing a rank for each material that equals the number of 1's in the logical AND. A word is preferably 32 bits.
3. Arranging the materials in rank order.
4. Computing whether it is possible to exceed the rank of the currently identified 25th ranked material by assuming that all the bits in the remaining words of the user defined indicator bitmap which were not matched in the first word would be matched in the remaining words of the record, and determining whether with this assumption the rank of the currently $25^{th}$ ranked material would be exceeded.
5. If not possible stop and report the top 25 materials, otherwise repeat steps 2, 3, 4 for the second word of each record and if necessary beyond to the third and forth word.

It has been found that in most cases it is not necessary to go beyond the first word, and that in most cases the performance is greatly speeded up, particularly on low speed palmtops and cell phones. When the process is complete, the results are reported in the results box 77. Note that to the left of each material is are a group of boxes 78 which give an indication of relative rank based on the number of boxes.

It will be appreciated that the preferred embodiments described provide a computer based apparatus for identifying hazardous materials based on their observable properties and signs and symptoms of exposure to them. Once a material is identified, the information needed for response to an incident involving the material can be obtained. The preferred embodiments can be operated on palm and handheld PDA's and similar devices as well as desktop computers. The preferred embodiments depend on converting data available in authoritative sources into useful information presented to a user in a form where he can make selections leading to a successful identification.

Although the present invention has been described in considerable detail with reference to certain preferred versions thereof, other versions are possible. Therefore the spirit and scope of the appended claims should not be limited to the preferred versions herein.

What is claimed is:

1. An apparatus for use in hazardous materials identification, comprising:
  a. a computer comprising an arithmetic processor unit, an output device, an input device and a computer memory;
  b. a first database comprising a multiplicity of records in the computer memory, wherein each of the multiplicity of records represents information about observable properties of one hazardous material, in the form of a bit sequence wherein each bit in the bit sequence can be assigned either a "present" value or an "absent" value and wherein each bit in the bit sequence represents a member of the group consisting of normalized descriptors of an observable property of a hazardous material, special modifiers, and unassigned positions;
  c. a computer representation in the computer memory, of response information relevant to use with the hazardous materials represented in the first sequential list;
  d. computer logic and resources adapted to
    i) display a plurality of property lists on the output device of the type from which a user can make selections, wherein each property list pertains to an observable property, and lists choices which are either normalized descriptors of the observable property or special modifiers pertaining to the observable property;
    ii) accept at least one selection from the user from the input device from at least one of the plurality of property lists said at least one selection being either a normalized descriptor or a special modifier and wherein the at least one selection may comprise a plurality of different selections;
    iii) store in the computer memory a user defined selection from each property list from which at least one selection was made in the form of a user defined descriptor bitmap;
    iv) evaluate a record in the first database to determine whether a hazardous material represented by the record is a possible matching hazardous material based on at least one bitwise comparison of each user defined selection with the record; and
    v) report the hazardous material on the output device if it is a possible matching hazardous material.

2. The apparatus of claim 1, wherein each of the multiplicity of records in the first database is a fixed length record, and each of the fixed length records has a sequential position in the computer memory so as to form a first sequential list wherein each of the fixed length records has a relative position within the first sequential list.

3. The apparatus of claim 2, wherein the computer logic and resources further comprise logic and resources to:
  a. find response information for the possible matching hazardous material using the relative position of the record, if requested by the user; and
  b. report the response information for the possible hazardous material on the output device, if requested by the user.

4. The apparatus of claim 3, wherein each of the multiplicity of records in the first database comprises a plurality of descriptor groups each descriptor group being made up of a bit sequence, and wherein each property list corresponds to a descriptor group and each choice on a property list corresponds to one bit in a descriptor group.

5. The apparatus of claim 4, wherein the first database is compiled by the acts of:
  a. contextually parsing plain language descriptions of a multiplicity of hazardous materials to identify a plurality of relevant descriptors and a plurality of modifiers pertaining to observable properties of the multiplicity of hazardous materials;

b. normalizing the plurality of descriptors and plurality of special modifiers into a common lexicon of normalized descriptors and special modifiers;

c. classifying each normalized descriptor and each special modifier into one of a plurality of descriptor groups, wherein at least one of the descriptor groups comprises a plurality of special modifiers;

d. assigning a binary power of 2 to each normalized descriptor and to each special modifier in each descriptor group, whereby each normalized descriptor and each special modifier in each descriptor group is represented by exactly one bit;

e. assigning an order to each of the plurality of descriptor groups, such that each fixed length record consists of a sequence of descriptor groups in the order; and f. assigning values to each descriptor group in each fixed length record that represents a hazardous material, such that the sequence of descriptor groups describes the hazardous material.

6. The apparatus of claim 5, wherein the plurality of property lists comprise three property lists and wherein the observable properties corresponding to the three property lists comprise color, texture, and odor.

7. The apparatus of claim 6, wherein the computer is a hand held computer having less than 16 MB of memory and wherein greater than 6000 hazardous materials and their response information can be identified and displayed.

8. The apparatus of claim 6, wherein the computer logic and resources to display a plurality of property lists comprises logic and resources to display each of the plurality of property lists in the form of pop-up menus.

9. The apparatus of claim 4, wherein the logic and resources to store in the computer memory a user defined selection from each property list from which at least one selection was made in the form of a user defined bitmap, is adapted to store the user defined selection in the form of a user defined bitmap comprising a user defined descriptor bitmap of normalized descriptors selected if any, and a user defined modifier bitmap which comprises a bitmap of special modifiers selected if any.

10. The apparatus of claim 9, wherein the logic and resources are adapted such that a fixed length record represents a possible matching hazardous material, if for each descriptor group in the fixed length record that corresponds to a property list from which at least one selection was made, there is at least one bit having the "present" value that corresponds to a selected bit, if any, in the user defined descriptor bitmap, and that there is at least one bit having the "present" value that corresponds to a selected bit, if any, in the user defined modifier bitmap.

11. The apparatus of claim 9, wherein the logic and resources are adapted such that a fixed length record represents a possible matching hazardous material, if for each descriptor group in the fixed length record that corresponds to a property list from which at least one selection was made, each selected bit in the user defined descriptor bitmap, if any, corresponds to a "present" value bit in the descriptor group, and each selected modifier in the user defined modifier bitmap if any, corresponds to a "present" value bit in the descriptor group.

12. The apparatus of claim 10, wherein the logic and resources to find a matching hazardous material further comprises logic and resources to evaluate each record in the first sequential list until every record has been examined.

13. The apparatus of claim 11, wherein the logic and resources further comprises logic and resources to evaluate each record in the first sequential list until every record has been examined.

14. The apparatus of claim 2, further comprising:

a. a second database comprising a second sequential list of fixed length records in the computer memory, wherein each fixed length record corresponds to a hazardous material and has a relative position in the second sequential list and wherein each fixed length record is a bit sequence in which each bit in the bit sequence represents an indicator of an exposure to a hazardous material and wherein every bit is either a "present" value or an "absent" value, and wherein every indicator is either a sign or a symptom;

b. computer logic and resources adapted to
  i) display indicators on the output device in the form of at least one list from which a user can make selections, wherein each indicator corresponds to a bit in the bit sequence;
  ii) accept at least one indicator selection from the user from the input device of a indicator wherein the at least one indicator selection may comprise a plurality of different selections;
  iii) store in the computer memory a user defined indicator bitmap corresponding to the at least one indicator selection; and
  iv) evaluate a record in the second sequential list of fixed length records by calculating a rank based on a bit wise comparison between the user defined indicator bitmap and the bit sequence.

15. The apparatus of claim 14 wherein the bit sequence in each record in the second sequential list is arranged in a manner related to frequency of occurrence of the corresponding indicator.

16. The apparatus of claim 15 wherein the logic and resources to evaluate a record are adapted such that the rank is the number of signs or symptoms in the user defined indicator bitmap which correspond to a "present" value bit in the bit sequence.

17. The apparatus of claim 16 wherein the logic and resources are adapted to report hazardous materials on the output device in an order of the rank of its corresponding record.

18. A computerized method for use in identifying a hazardous material on a computer having an output device, an input device and a computer memory comprising the steps of:

a. storing a first sequential list comprising a multiplicity of fixed length records in the computer memory, wherein each fixed length record has a relative position in the first sequential list and represents a hazardous material, and each fixed length record consists of a bit sequence wherein each bit can be assigned either a "present" value or an "absent" value wherein each bit represents a member of the group consisting of normalized descriptors of an observable property of a hazardous material, special modifiers, and unassigned positions;

b. storing a computer representation in the computer memory, of response information relevant to use with the hazardous materials represented in the first sequential list;

c. displaying a plurality of property lists on the computer output device of the type from which a user can make selections, wherein each property list pertains to an observable property, and lists choices which are either normalized descriptor of the observable property or special modifiers pertaining to the observable property;

d. accepting at least one selection from a user from the computer input device from at least one of the plurality of property lists the at least one selection being either a normalized descriptor or a special modifier wherein the at least one selection may comprise a plurality of different selections;

e. storing in the computer memory a user defined selection from each property list from which at least one selection was made wherein each user defined selection comprises a user defined descriptor bitmap which comprises a bitmap of normalized descriptors selected, if any, and a user defined modifier bitmap which comprises a bit map of special modifiers selected, if any;

f. evaluating a record in the first sequential list of fixed length records to determine whether a hazardous material represented by the record is a possible matching hazardous material based on at least one bit wise comparison of each user defined selection with the record;

g. reporting the hazardous material on the output device if it is a possible matching hazardous material;

h. finding response information for a possible matching hazardous material using the relative position of the record if requested by the user; and i. reporting the response information for the possible hazardous material on the output device.

19. The method of claim 18, wherein the step of displaying a plurality of property lists further comprises displaying each of the plurality of property lists in the form of pop up menus.

20. The method of claim 18, wherein the plurality of property lists comprise three property lists.

21. The method of claim 20, wherein the observable properties corresponding to the three property lists comprise color, texture, and odor.

22. The method of claim 18, wherein each fixed length record in the first sequential list, comprises a plurality of descriptor groups and wherein each property list corresponds to a descriptor list and each choice on a property list corresponds to one bit in the descriptor list.

23. The method of claim 22, wherein storing a first sequential list further comprises the following acts:

a. contextually parsing plain language descriptions of a multiplicity of hazardous materials to identify a plurality of relevant descriptors and a plurality of modifiers pertaining to observable properties of the multiplicity of hazardous materials;

b. normalizing the plurality of descriptors and plurality of special modifiers into a common lexicon of normalized descriptors and special modifiers;

c. classifying each normalized descriptor and each special modifier into one of a plurality of descriptor groups, wherein at least one of the descriptor groups comprises a plurality of special modifiers;

d. assigning a binary power of 2 to each normalized descriptor and to each special modifier in each descriptor group, whereby each normalized descriptor and each special modifier in each descriptor group is represented by exactly one bit;

e. assigning an order to each of the plurality of descriptor groups, such that each fixed length record consists of a sequence of descriptor groups in the order; and f. assigning values to each descriptor group in each fixed length record that represents a hazardous material, such that the sequence of descriptor groups describes the hazardous material.

24. The method of claim 23, wherein a fixed length record represents a possible matching hazardous material, if for each descriptor group in the fixed length record that corresponds to a property list from which at least one selection was made, there is at least one bit with "present" value that corresponds to a selected bit, if any, in the user defined descriptor bitmap, and that there is at least one bit with the "present" value that corresponds to a selected bit, if any, in the user defined modifier bitmap.

25. The method of claim 23, wherein a fixed length record represents a possible matching hazardous material, if for each descriptor group in the fixed length record that corresponds to a property list from which at least one selection was made, each selected bit in the user defined descriptor bitmap, if any, corresponds to a "present" value bit in the descriptor group, and each selected bit in the user defined modifier bitmap, if any, corresponds to a "present" value bit in the descriptor group.

26. The method of claim 18, further comprising the steps of:

a. loading a second sequential list of fixed length records into the computer memory, wherein each fixed length record corresponds to a hazardous material and has a relative position in the second sequential list and wherein each fixed length record is a bit sequence in which each bit in the bit sequence represents either a normalized sign or symptom of an exposure to a hazardous material and wherein every bit has either a "present" value or an "absent" value;

b. displaying signs and symptoms on an output device in the form of at least one list from which a user can make selections, wherein each sign and each symptom corresponds to a bit in the bit sequence;

c. accepting at least one selection from the user from the input device of a sign or symptom wherein the at least one selection may comprise a plurality of different selections;

d. storing in computer memory a user defined sign symptom bitmap corresponding to the at least one sign symptom selection; and e. evaluating a record in the second sequential list of fixed length records by calculating a rank based on a bit wise comparison between the user defined sign symptom bitmap and the bit sequence of the record.

27. The method of claim 26, wherein the bit sequence in each record in the second sequential list is arranged in a manner related to frequency of occurrence of the corresponding sign or symptom.

28. The method of claim 27, wherein calculating a rank comprises computing the number of bits in the user defined sign symptom bitmap which correspond to a "present" value bit in the bit sequence of the record.

29. The method of claim 28, further comprising reporting hazardous materials on the output device in an order of the rank of its corresponding record.

30. Instructions in computer usable form which carry out the method of claim 18.

31. Instructions in computer usable form which carry out the method of claim 26.

32. The instructions of claim 30 wherein the computer usable form is computer readable form.

33. The instructions of claim 31 wherein the computer usable form is computer readable form.

* * * * *